（12） United States Patent
Mittal

(10) Patent No.: US 9,113,777 B2
(45) Date of Patent: Aug. 25, 2015

(54) ULTRA LOW POWER PLATFORM FOR REMOTE HEALTH MONITORING

(71) Applicant: BIOBIT INC., Palo Alto, CA (US)

(72) Inventor: Rohit Mittal, Sunnyvale, CA (US)

(73) Assignee: Biobit Inc., Palo Alto, CA (US)

( * ) Notice: Subject to any disclaimer, the term of this patent is extended or adjusted under 35 U.S.C. 154(b) by 0 days.

(21) Appl. No.: 14/011,681

(22) Filed: Aug. 27, 2013

(65) Prior Publication Data

US 2014/0296678 A1    Oct. 2, 2014

Related U.S. Application Data

(60) Provisional application No. 61/852,967, filed on Mar. 26, 2013.

(51) Int. Cl.
*A61B 5/04* (2006.01)
*A61N 1/00* (2006.01)
*A61B 5/00* (2006.01)

(52) U.S. Cl.
CPC ............. *A61B 5/0022* (2013.01); *A61B 5/7232* (2013.01); *A61B 5/04* (2013.01)

(58) Field of Classification Search
USPC ...................... 600/508–509; 607/60
See application file for complete search history.

(56) References Cited

U.S. PATENT DOCUMENTS

| | | | | |
|---|---|---|---|---|
| 5,836,982 | A * | 11/1998 | Muhlenberg et al. | 607/9 |
| 2002/0026122 | A1 * | 2/2002 | Lee et al. | 600/523 |
| 2011/0082377 | A1 * | 4/2011 | Mahajan et al. | 600/508 |

OTHER PUBLICATIONS

Candes, Emmanuel J. and Wakin, Michael B., An Introduction to Compressive Sampling, IEEE Signal Processing Magazine, Mar. 2008, pages, pp. 21-30.

* cited by examiner

*Primary Examiner* — Nicole F Lavert
(74) *Attorney, Agent, or Firm* — Mattingly & Malur, PC

(57) ABSTRACT

An apparatus and method is described to sense sparse signals from a medical device using compressed sensing and then transmitting the data for processing in the cloud.

20 Claims, 6 Drawing Sheets

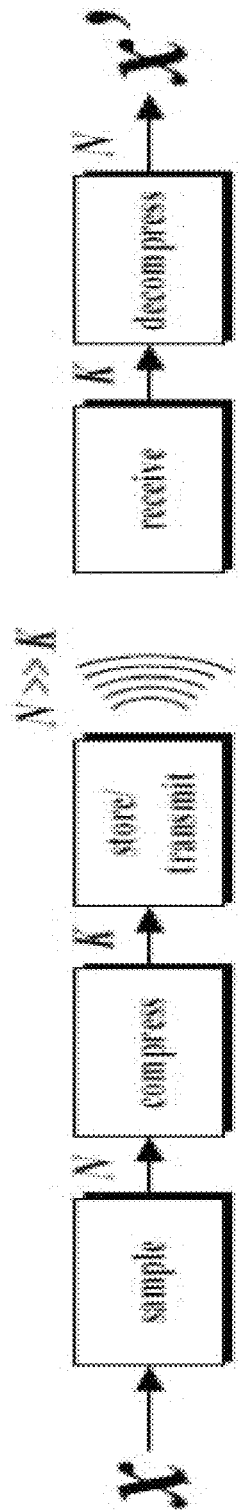
FIGURE 4a (Prior Art): Traditional Nyquist Sampling
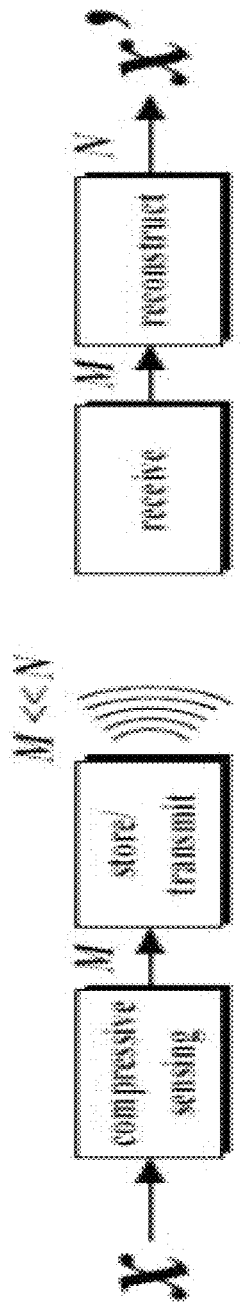
FIGURE 4b (Prior Art): Compressed Sensing

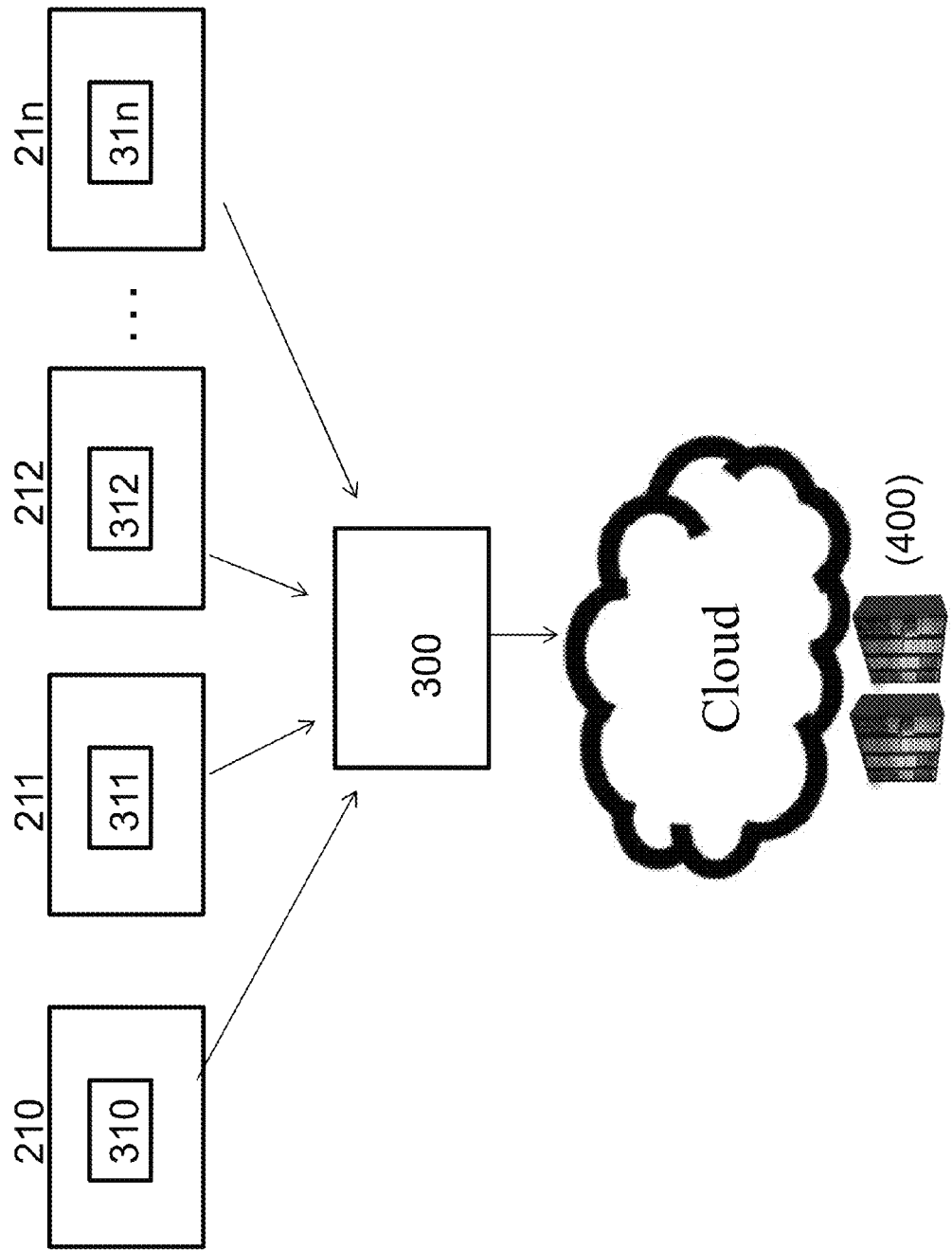

ULTRA LOW POWER PLATFORM FOR REMOTE HEALTH MONITORING

PRIORITY CLAIM

This application claims the benefit under 35 USC 119(e) to U.S. Provisional Patent Application Ser. No. 61/852,967, filed on Mar. 26, 2013 and titled "A compressed sensor platform for remote health monitoring," which is incorporated by reference herein.

TECHNICAL FIELD

The present invention relates to the field of sensor implementations. In particular, an apparatus and method is described to sense sparse signals from a medical device using compressed sensing and then transmitting the data for processing in the cloud.

BACKGROUND OF THE INVENTION

A typical prior art sensor network used for remote health monitoring is depicted in FIG. 1. The two main components are sensor block 200 and computing device 300, which here is an intelligent backend device. Sensor block 200 typically is a medical device for obtaining data from a patient, such as an electroencephalograph, cardiotocograph, or other device. Sensor block 200 comprises an amplifier (100), an analog-to-digital (ADC) conversion block 101, a post processor 102, a transmitter 103, and an antenna 104. It is to be understood that other sensor blocks similar to sensor block 200 can be used with the same computing device 300. For brevity's sake, only sensor block 200 is depicted in FIG. 1.

Computing device 300 may be a PC, server or any product with processing capabilities. Sensor block 200 obtains data from a patient, such as brain signals, heart signals, temperature, etc. using electrodes or other means, amplifies the sensed analog signals using amplifier 100, converts the analog signal into digital data using analog-to-digital conversion block 101, and processes the raw digital data using post processor 102, which can packetize the data, add headers, encrypt the data, and perform other known techniques. The packetized data is then send to computing device using transmitter 103 and antenna 104 over network 105. Network 105 can be a wireless network, a hardwired network, or a combination of the two.

The prior art sensor network of FIG. 1 has several drawbacks. First, sensor block 200 consumes a substantial amount of power. This is mainly because the sensor runs at full speed. As an example, if sensor block 200 is generating electroencephalography (EEG) signals, the signal bandwidth will include frequencies up to 1 KHz, and analog-to-digital converter 20 will need to perform sampling of the analog signal at a rate of at least 2 KHz (which is the Nyquist rate of the highest frequency in the signal). In addition, transmitter 103 will needs to transmit at that same rate, 2 KHz. In a typical medical device, transmitter 103 can consume 80% of the total power consumed by the device. For some applications where packetization and encryption needs are large, the post processing block may be the power bottleneck since it too runs at or above the Nyquist rate.

Second, computing device 300 needs to store all the data it receives and process it. Typically the computing device 300 will process the received data and take actions in response to the data (for example, begin an audio alarm). It can be appreciated that computing device 300 performs a substantial amount of data analysis and typically will generate a user interface that creates a visual display of the data obtained by sensor block 200. The large amount of data leads to high storage costs and consumes a significant amount of processing time and power.

Third, security is a major implementation drain. Sending data over wireless links requires some mode of encryption, all of which require extra power and resources.

What is needed is an improved sensor network that with sensor blocks that transmit less data and a computing device that operates on less data than in prior art sensor networks.

SUMMARY OF THE INVENTION

The aforementioned problem and needs are addressed through an embodiment that utilized compressed sensing within the sensor block. Compressed sensing can be used to process analog signals that are sparse in nature, meaning that the signal is periodic and does not change significantly over time. The human body naturally generates many signals that are sparse in nature, such as heart beat, brainwaves, etc.

BRIEF DESCRIPTION OF THE DRAWINGS

FIG. 4a depicts the prior art Nyquist method.
FIG. 4b depicts the prior art compressed sensing method.
FIG. 5 depicts an embodiment of a sensor network utilizing compressed sensing used with a Body Area Network.

DETAILED DESCRIPTION OF THE PREFERRED EMBODIMENTS

Figure 2:
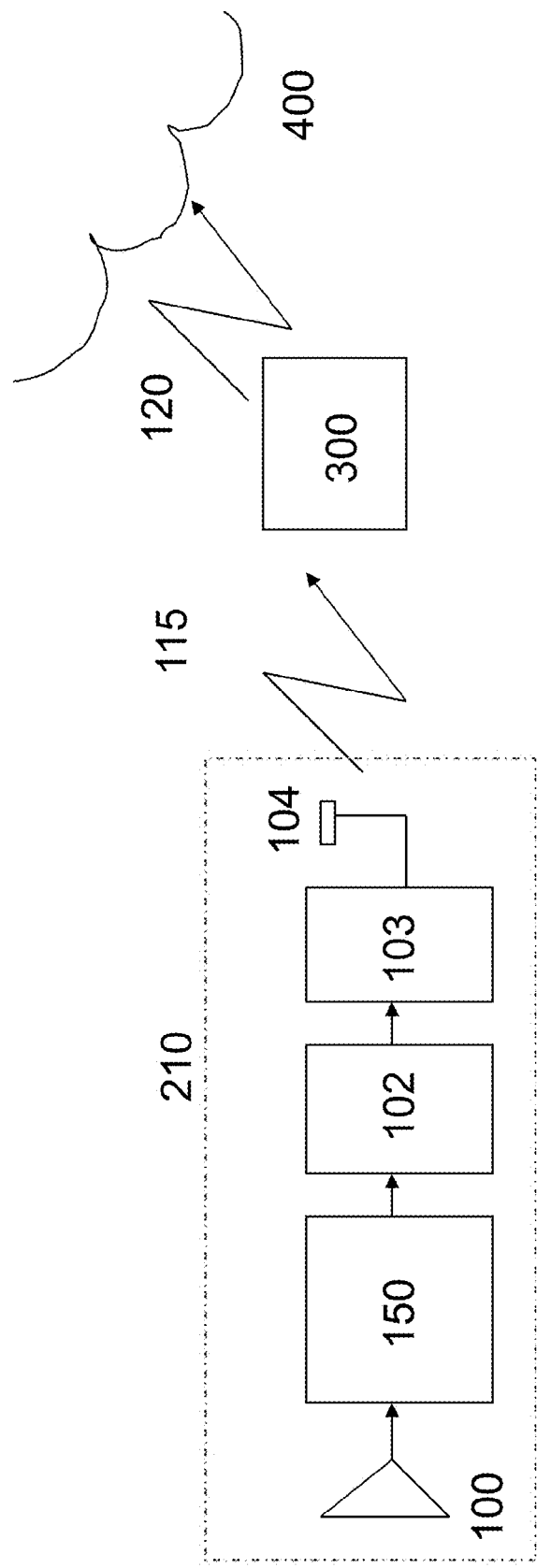
FIG. 2 depicts an embodiment of a sensor network utilizing compressed sensing and a cloud.

To solve the issues outlined in the prior art section, a new platform sensor network is shown in FIG. 2. Sensor block 210 shares certain blocks with prior art sensor block 200. Namely, sensor block 210 comprises amplifier 100, post processor 102, transmitter 103, and antenna 104. However, unlike the prior art sensor block 200, sensor block 210 contains compressed sensing analog-to-digital conversion block 150. It is to be understood that other sensor blocks similar to sensor block 210 can be used with the same computing device 300. For brevity's sake, only sensor block 210 is depicted in FIG. 2. Compressed sensing is a known technique in other fields. A seminal paper on compressed sensing is "An Introduction to Compressive Sampling," Emmanuel J. Candes and Michael B. Wakin, IEEE Signal Processing Magazine, March 2008, which is incorporated by reference herein.

Sensor block 210 communicates with computing device 300 over network 115. Computing device 300 can communicate with the cloud 400 over network 120. Network 115 and network 120 each can comprise a wireless or hardwired network or a combination of the two. Network 115 preferably is a cellular network, such as a 3G or 4G network, and transmitter 103 is capable of transmitting signals over such a network.

In one embodiment, amplifier 100 is implemented as a switched capacitor amplifier with a chopper or other means of mitigating 1/f noise Amplifier 100 optionally can be coupled to one or more electrodes used to measure electrical data directly from a human patient. Compressed sensing analog-to-digital conversion block 150 can be implemented using a switched capacitor multiplier. Post processor 102 can be implemented as a programmable state machine which can be configurable for various standards and security requirements. Transmitter 103 can be an ultra low power switched capacitor class C amplifier. In this way the whole system can be implemented with a CMOS ASIC and a few external components such as antenna and bio-medical tissue interface.

Figure 3:
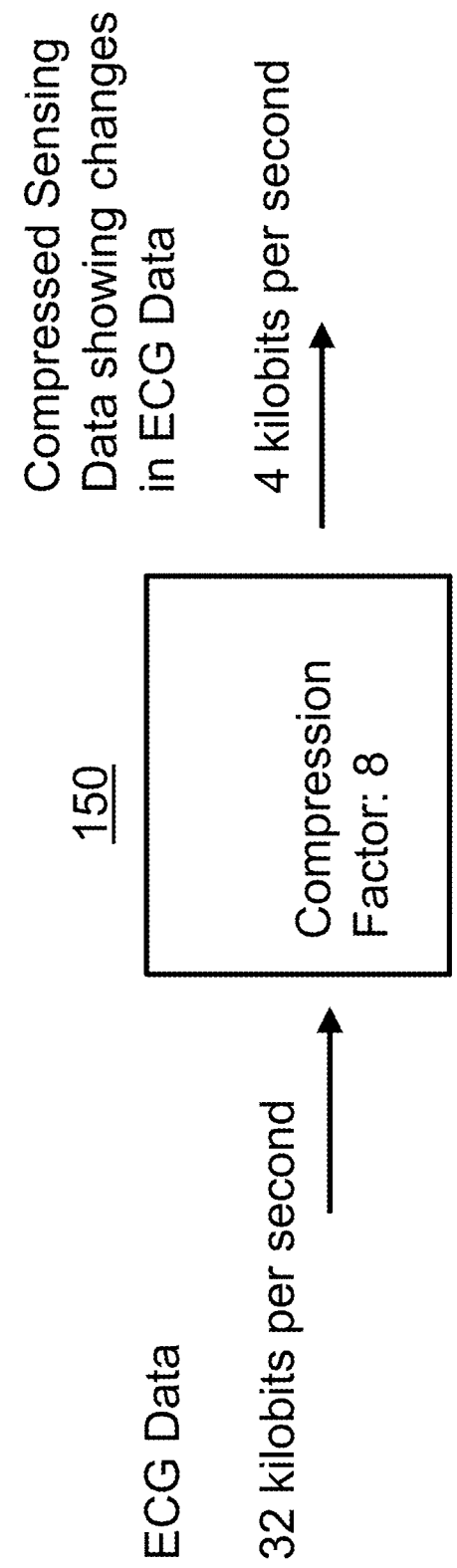
FIG. 3 depicts an embodiment of a compressed sensing analog-to-digital conversion block.

Additional detail regarding compressed sensing analog-to-digital conversion block 150 is shown in FIG. 3 and FIGS. 4*a* and 4*b*. FIG. 4*a* depicts the traditional Nyquist sampling method, and FIG. 4*b* depicts the more recently developed compressed sensing method. By not having to store a lot of data (as is the case in FIG. 4*a* and Nyquist sampling), and then discarding it, compressed sensing, as depicted in FIG. 4*b*, saves valuable power in the way it performs compression. Compressed sensing is a relatively new phenomenon that uses knowledge of signal sparsity. The compressed sensing front end will require a randomization matrix to mix with the input signal. This will spread the frequency content of the signal and prevent eavesdropping, much like with spread spectrum communication.

Figure 1:
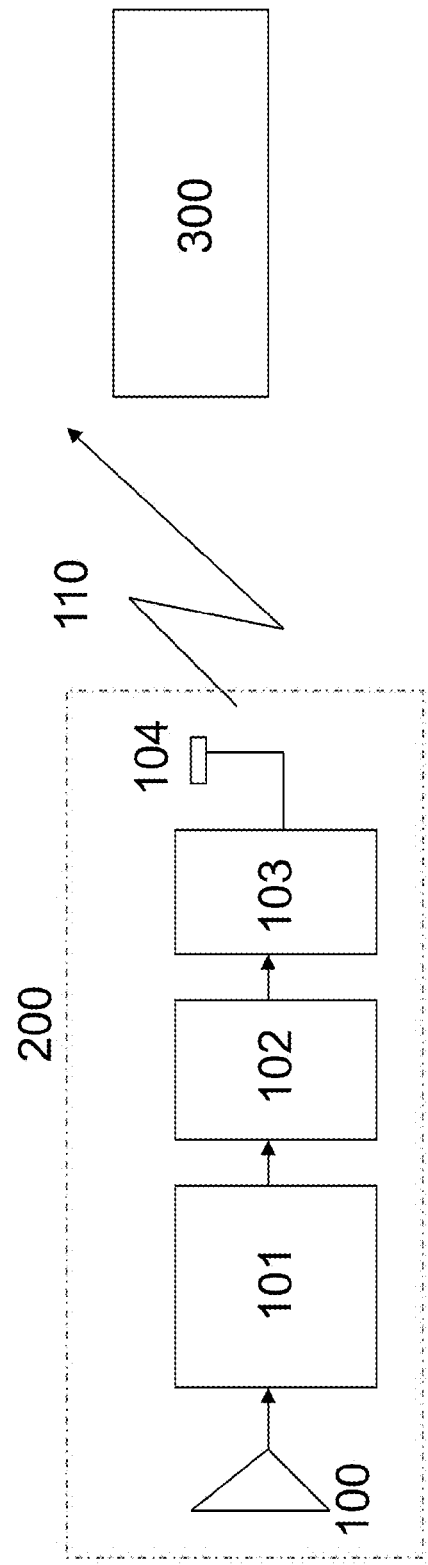
FIG. 1 depicts a prior art sensor network.

By utilizing compressed sensing analog-to-digital conversion block 150, the sensor network of FIGS. 2 and 3 will use substantially less power than the prior art sensor network of FIG. 1. The compressed sensing analog-to-digital conversion block 150 relies upon an inherent sparsity of an input signal received from the amplifier 100, without prior knowledge of the input signal, for sampling of the input signal below the Nyquist rate to reduce power. The sampling rate of both the compressed sensing analog-to-digital conversion block 150 and transmitter 103 is reduced by the compression factor when compared to analog-to-digital conversion block 101 and transmitter 103 of sensor block 200. This leads to a direct savings in power. Post processor 102 will also operate on less data in sensor block 210 than in sensor block 200, leading to further power savings. With reference to FIG. 3, compressed sensing analog-to-digital conversion block 150 can utilize a compression rate of 8×-16×, which will lead to a similar decrease in power consumption for sensor block 210 compared to prior art sensor block 200.

Portions of the article "An Introduction to Compressive Sampling," Emmanuel J. Candes and Michael B. Wakin, IEEE Signal Processing Magazine, March 2008, which is incorporated by reference herein, are explicitly set forth below:

Conventional approaches to sampling signals or images follow Shannon's celebrated theorem: the sampling rate must be at least twice the maximum frequency present in the signal (the so-called Nyquist rate). In fact, this principle underlies nearly all signal acquisition protocols used in consumer audio and visual electronics, medical imaging devices, radio receivers, and so on. (For some signals, such as images that are not naturally bandlimited, the sampling rate is dictated not by the Shannon theorem but by the desired temporal or spatial resolution. However, it is common in such systems to use an antialiasing low-pass filter to band limit the signal before sampling, and so the Shannon theorem plays an implicit role.) In the field of data conversion, for example, standard analog-to-digital converter (ADC) technology implements the usual quantized Shannon representation: the signal is uniformly sampled at or above the Nyquist rate. (IEEE Signal Processing Magazine March 2008, page 21).

This article surveys the theory of compressive sampling, also known as compressed sensing or CS, is a novel sensing/sampling paradigm that goes against the common wisdom in data acquisition. CS theory asserts that one can recover certain signals and images from far fewer samples or measurements than traditional methods use. To make this possible, CS relies on two principles: sparsity, which pertains to the signals of interest, and incoherence, which pertains to the sensing modality.

Sparsity expresses the idea that the "information rate" of a continuous time signal may be much smaller than suggested by its bandwidth, or that a discrete-time signal depends on a number of degrees of freedom which is comparably much smaller than its (finite) length. More precisely, CS exploits the fact that many natural signals are sparse or compressible in the sense that they have concise representations when expressed in the proper basis $\Psi$.

Incoherence extends the duality between time and frequency and expresses the idea that objects having a sparse representation in $\Psi$ must be spread out in the domain in which they are acquired, just as a Dirac or a spike in the time domain is spread out in the frequency domain. Put differently, incoherence says that unlike the signal of interest, the sampling/sensing waveforms have an extremely dense representation in $\Psi$.

The crucial observation is that one can design efficient sensing or sampling protocols that capture the useful information content embedded in a sparse signal and condense it into a small amount of data. These protocols are nonadaptive and simply require correlating the signal with a small number of fixed waveforms that are incoherent with the sparsifying basis. What is most remarkable about these sampling protocols is that they allow a sensor to very efficiently capture the information in a sparse signal without trying to comprehend that signal. Further, there is a way to use numerical optimization to reconstruct the full-length signal from the small amount of collected data. In other words, CS is a very simple and efficient signal acquisition protocol which samples—in a signal independent fashion—at a low rate and later uses computational power for reconstruction from what appears to be an incomplete set of measurements. (IEEE Signal Processing Magazine March 2008, page 22, left column).

Incoherence and Sensing of Sparse Signals

This section presents the two fundamental premises underlying CS: sparsity and incoherence.

Sparsity

Many natural signals have concise representations when expressed in a convenient basis. Consider, for example, the image in FIG. 1(*a*) and its wavelet transform in (*b*). Although nearly all the image pixels have nonzero values, the wavelet coefficients offer a concise summary: most coefficients are small and the relatively few large coefficients capture most of the information . . . . In plain terms, one can "throw away" a large fraction of the coefficients without much loss. FIG. 1(*c*) shows an example where the perceptual loss is hardly noticeable from a megapixel image to its approximation obtained by throwing away 97.5% of the coefficients.

This principle is, of course, what underlies most modern lossy coders such as JPEG-2000 [4] and many others, since a simple method for data compression would be to compute x from f and then (adaptively) encode the locations and values of the S significant coefficients. Such a process requires knowledge of all the n coefficients x, as the locations of the significant pieces of information may not be known in advance (they are signal dependent); in our example, they tend to be clustered around edges in the image. More generally, sparsity is a fundamental modeling tool which permits efficient fundamental signal processing; e.g., accurate statistical estimation and classification, efficient data compression, and so on. This article is about a more surprising and far-reaching implication, however, which is that sparsity has significant bearings on the acquisition process itself. Sparsity determines how efficiently one can acquire signals nonadaptively. (IEEE Signal Processing Magazine March 2008, page 23, left and right column).

Incoherent Sampling

... In plain English, the Coherence measures the largest correlation between any two elements of the sensing basis φ and the representation basis Ψ; see also [5]. If φ and Ψ contain correlated elements, the coherence is large. Otherwise, it is small ... CS is mainly concerned with low coherence pairs. (IEEE Signal Processing Magazine March 2008, page 23, right column).

We wish to make three comments:
1) The role of the coherence is completely transparent; the smaller the coherence, the fewer samples are needed, hence our emphasis on low coherence systems in the previous section.
2) One suffers no information loss by measuring just about any set of m coefficients which may be far less than the signal size apparently demands. If $\mu(\phi, \Psi)$ is equal or close to one, then on the order of S log n samples suffice instead of n.
3) The signal f can be exactly recovered from our condensed data set by minimizing a convex functional which does not assume any knowledge about the number of nonzero coordinates of x, their locations, or their amplitudes which we assume are all completely unknown a priori. We just run the algorithm and if the signal happens to be sufficiently sparse, exact recovery occurs.

The theorem indeed suggests a very concrete acquisition protocol: sample nonadaptively in an incoherent domain and invoke linear programming after the acquisition step. Following this protocol would essentially acquire the signal in a compressed form. All that is needed is a decoder to "decompress" this data; this is the role of l1 minimization. (IEEE Signal Processing Magazine March 2008, page 24, right column).

This example shows that a number of samples just about 4× the sparsity level suffices. Many researchers have reported on similar empirical successes. There is de facto a known four-to-one practical rule which says that for exact recovery, one needs about four incoherent samples per unknown nonzero term. (IEEE Signal Processing Magazine March 2008, page 26, left column).

What is Compressive Sampling?

Data acquisition typically works as follows: massive amounts of data are collected only to be—in large part—discarded at the compression stage to facilitate storage and transmission. In the language of this article, one acquires a high-resolution pixel array f, computes the complete set of transform coefficients, encode the largest coefficients and discard all the others, essentially ending up with fS. This process of massive data acquisition followed by compression is extremely wasteful (one can think about a digital camera which has millions of imaging sensors, the pixels, but eventually encodes the picture in just a few hundred kilobytes). CS operates very differently, and performs as "if it were possible to directly acquire just the important information about the object of interest." By taking about O(S log(n/S)) random projections as in "Random Sensing," one has enough information to reconstruct the signal with accuracy at least as good as that provided by fS, the best S-term approximation—the best compressed representation—of the object. In other words, CS measurement protocols essentially translate analog data into an already compressed digital form so that one can—at least in principle—obtain super-resolved signals from just a few sensors. All that is needed after the acquisition step is to "decompress" the measured data. (IEEE Signal Processing Magazine March 2008, page 28, left column).

Applications

The fact that a compressible signal can be captured efficiently using a number of incoherent measurements that is proportional to its information level S<<n has implications that are far reaching and concern a number of possible applications. (IEEE Signal Processing Magazine March 2008, page 28, right column).

The point here is that even though the amount of data is ridiculously small, one has nevertheless captured most of the information contained in the signal. This, in a nutshell, is why CS holds such great promise. (IEEE Signal Processing Magazine March 2008, page 30, left column).

In another embodiment, to further reduce power, post processor 102 or transmitter 103 can queue the packets of compressed data in memory and then transmit in burst mode instead of in a continual fashion.

The proposed network helps in managing "big data." Big data consists of 3 components: velocity, volume and value. In the embodiment of FIG. 2, computing device 300 is connected to cloud 400 where the data is extracted in the raw form for processing. In this embodiment, the data is processed by cloud computing device 400 and not computing device 300. Because computing device 300 does not perform the data extraction and processing, it too can be optimized for low power consumption. Using compressed sensing will lower the storage cost for the data by as much as 10×-20×.

Figure 6:
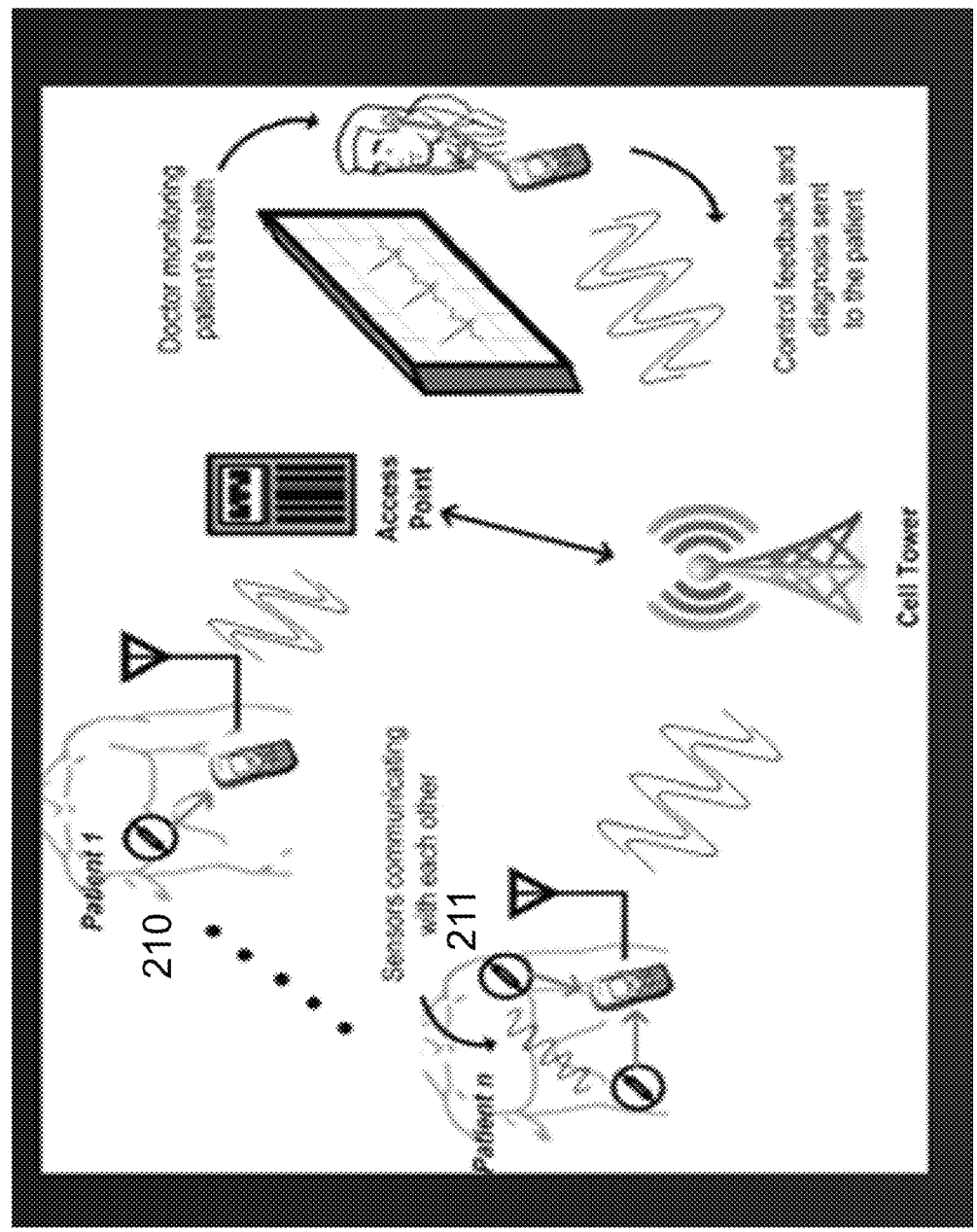
FIG. 6 depicts an embodiment of a sensor network utilizing compressed sensing used with a Body Area Network.

FIGS. 5 and 6 show an application of the invention to body area networks. The data is transmitted from sensor block 210, sensor block 211, sensor block 212, and any number of other sensor blocks 21n, using the same functional design of sensor block 210 shown in FIGS. 2 and 3. Here, sensor block 210 comprises EEG (electroencephalography) electrodes 310 for obtaining electrical data from a human patient's scalp, sensor block 211 comprises ECG (electrocardiography) electrodes 311 for obtaining electrical data from a human patient's heart, and sensor block 212 comprises CTG (cardiotocography) electrodes 312 for obtaining electrical data from human patient's uterine contractions and fetal heartbeat. Sensor block 21n comprises electrodes 31n, or other physical sensors, for obtaining other medical or biological data from a human patient.

Computing device 300 here is a smart phone. Computing device 300 optionally comprises a software application that enables a user of computing device 300 to view graphical or numerical representations of the data collected by sensor block 210, sensor block 211, and other sensor blocks 21n. Concurrently, the data will be transmitted to cloud computing device 400 where it can be processed.

References to the present invention herein are not intended to limit the scope of any claim or claim term, but instead merely make reference to one or more features that may be covered by one or more of the claims. Materials, processes and numerical examples described above are exemplary only, and should not be deemed to limit the claims. It should be noted that, as used herein, the terms "over" and "on" both inclusively include "directly on" (no intermediate materials, elements or space disposed there between) and "indirectly on" (intermediate materials, elements or space disposed there between). Likewise, the term "adjacent" includes "directly adjacent" (no intermediate materials, elements or space disposed there between) and "indirectly adjacent" (intermediate materials, elements or space disposed there between). For example, forming an element "over a substrate" can include forming the element directly on the substrate with no intermediate materials/elements there between, as well as forming the element indirectly on the substrate with one or more intermediate materials/elements there between.

What is claimed is:

1. A sensor block for collecting data from a human patient, comprising:
   an amplifier;
   a compressed sensing analog-to-digital conversion block coupled to the amplifier; the compressed sensing analog-to-digital conversion block relying upon an inherent sparsity and incoherence of an input signal received from the amplifier, without prior knowledge of the input signal, for sampling of the input signal below the Nyquist rate to reduce power;
   a post processor coupled to the compressed sensing analog-to-digital conversion block;
   a transmitter coupled to the post processor; and
   an antenna.

2. The sensor block of claim 1, wherein the compressed sensing analog-to-digital conversion block comprises a random number generator for encrypting data.

3. The sensor block of claim 1, wherein the compressed sensing analog-to-digital conversion block utilizes a compression factor of at least 8.

4. The sensor block of claim 1, wherein the sensor block further comprises electroencephalography electrodes.

5. The sensor block of claim 1, wherein the sensor block further comprises electrocardiography electrodes.

6. The sensor block of claim 1, wherein the sensor block further comprises cardiotocography electrodes.

7. A body area network for collecting and processing data from a human patient, comprising:
   a sensor block comprising:
      an amplifier;
      a compressed sensing analog-to-digital conversion block coupled to the amplifier, the compressed sensing analog-to-digital conversion block relying upon an inherent sparsity and incoherence of an input signal received from the amplifier, without prior knowledge of the input signal, for sampling of the input signal below the Nyquist rate to reduce power;
      a post processor coupled to the compressed sensing analog-to-digital conversion block;
      a transmitter coupled to the post processor; and
      an antenna;
   a smartphone coupled to the sensor block over a wireless network; and
   a cloud computing device coupled to the smartphone over another wireless network.

8. The body area network of claim 7, wherein the compressed sensing analog-to-digital conversion block comprises a random number generator for encrypting data.

9. The body area network of claim 7, wherein the compressed sensing analog-to-digital conversion block utilizes a compression factor of at least 8.

10. The body area network of claim 7, wherein the sensor block further comprises electroencephalography sensors.

11. The body area network of claim 7, wherein the sensor block further comprises electrocardiography sensors.

12. The body area network of claim 7, wherein the sensor block further comprises cardiotocography sensors.

13. A method of collecting and processing data from a human patient, the method comprising the steps of:
   obtaining data from the human patient using electrodes;
   generating compressed data using a compressed sensing analog-to-digital conversion block operating on the data from the human patient, the compressed sensing analog-to-digital conversion block relying upon an inherent sparsity and incoherence of an input signal received from the amplifier, without prior knowledge of the input signal, for sampling of the input signal below the Nyquist rate to reduce power;
   processing the compressed data using a post processor to generate processed data;
   transmitting the processed data to a smartphone over a wireless network; and
   transmitting the processing data from the smartphone to a cloud computing device over another wireless network.

14. The method of claim 13, wherein the data from the human patient comprises electroencephalography data.

15. The method of claim 13, wherein the data from the human patient comprises electrocardiography data.

16. The method of claim 13, wherein the data from the human patient comprises cardiotocography data.

17. The method of claim 13, further comprising the step of:
   generating graphical representations of the processed data on the smartphone.

18. The method of claim 17, further comprising the step of:
   generating numerical representations of the processed data on the smartphone.

19. The method of claim 13, further comprising the step of:
   queuing packets of processed data in a memory.

20. The method of claim 19, wherein the step of transmitting the processed data to a smartphone comprises transmitting packets of processed data in a burst mode.

* * * * *